US008829215B2

(12) United States Patent
Breivik et al.

(10) Patent No.: US 8,829,215 B2
(45) Date of Patent: Sep. 9, 2014

(54) KRILL OIL PROCESS

(75) Inventors: Harald Breivik, Porsgrunn (NO); Olav Thorstad, Porsgrunn (NO)

(73) Assignee: Pronova Biopharma Norge AS, Baerum (NO)

( * ) Notice: Subject to any disclaimer, the term of this patent is extended or adjusted under 35 U.S.C. 154(b) by 734 days.

(21) Appl. No.: 12/992,365

(22) PCT Filed: May 15, 2009

(86) PCT No.: PCT/NO2009/000184
§ 371 (c)(1),
(2), (4) Date: Feb. 11, 2011

(87) PCT Pub. No.: WO2009/139641
PCT Pub. Date: Nov. 19, 2009

(65) Prior Publication Data
US 2011/0130458 A1    Jun. 2, 2011

Related U.S. Application Data

(60) Provisional application No. 61/053,455, filed on May 15, 2008.

(51) Int. Cl.
| | | |
|---|---|---|
| C11B 1/00 | (2006.01) | |
| A23L 1/30 | (2006.01) | |
| A23D 9/02 | (2006.01) | |
| C11B 1/10 | (2006.01) | |
| A61K 35/56 | (2006.01) | |
| C11B 3/12 | (2006.01) | |
| C11B 7/00 | (2006.01) | |
| C11B 1/02 | (2006.01) | |
| A23D 9/013 | (2006.01) | |

(52) U.S. Cl.
CPC .............. *C11B 1/104* (2013.01); *A23L 1/3008* (2013.01); *A23D 9/02* (2013.01); *C11B 1/10* (2013.01); *A61K 35/612* (2013.01); *C11B 3/12* (2013.01); *C11B 7/0083* (2013.01); *C11B 1/02* (2013.01); *A23D 9/013* (2013.01)
USPC .......................................................... 554/18

(58) Field of Classification Search
USPC .......................................................... 554/18
See application file for complete search history.

(56) References Cited

U.S. PATENT DOCUMENTS

| | | | |
|---|---|---|---|
| 4,377,526 A | 3/1983 | Fujita et al. | |
| 6,800,299 B1 | 10/2004 | Beaudoin et al. | |
| 2007/0141949 A1 | 6/2007 | Yoshitomi | |

FOREIGN PATENT DOCUMENTS

| | | |
|---|---|---|
| CA | 1098900 A | 4/1981 |
| JP | 54-76858 | 6/1979 |
| JP | 58-8037 | 1/1983 |
| JP | 63-162793 | 7/1988 |
| JP | 1304852 A | 12/1989 |
| JP | 02-215351 | 8/1990 |
| JP | 2215351 * | 8/1990 |
| JP | 2215351 A | 8/1990 |
| JP | 04-41457 | 2/1992 |
| JP | 06-248289 | 9/1994 |
| JP | 08-218091 | 8/1996 |
| JP | 2005-245379 | 9/2005 |
| JP | 2006115750 A | 5/2006 |
| RU | 2000066 C | 9/1993 |
| RU | 2034492 C1 | 5/1995 |
| RU | 2266949 C1 | 12/2005 |
| WO | WO 00/23546 A1 | 4/2000 |
| WO | WO 2004/047554 A1 | 6/2004 |
| WO | WO 2006/106325 A1 | 10/2006 |
| WO | WO 2007/080514 A2 | 7/2007 |
| WO | WO 2008/050219 A2 | 5/2008 |
| WO | WO 2008/060163 A1 | 5/2008 |

OTHER PUBLICATIONS

English abstract of JP 1304852 A, WPI Database Week 199004.
English abstract of JP 2215351 A, CAPLUS 1991:36017.
English abstract of JP 2006115750, A WPI Database Week 200633.
English abstract of RU 2000066 C, Basic Derwent Week 199406.
English abstract of RU 2034492 C1, WPI Database Week 199602.
English abstract of RU 2266949 C1, Basic Derwent Week 200607.
Hwang, L.S. et al., "Fractionation of urea pretreated squid visceral oil ethyl esters," *J. Am. Oil Chem. Soc.* (2001) vol. 78, pp. 473-476.
International Search Report for PCT/NO2007/000402 (WO 2008/060163 A9, Revised Version) dated May 22, 2008 (6 pages).
International Search Report for PCT/NO2009/000184 (WO 2009/139641 A1) dated Aug. 18, 2009 (6 pages).
Lapin, B.P. et al., "Separation of lipophilic fractions by high-performance liquid chromatorgraphy," *J. Chromatogr.* (1986) vol. 365, pp. 229-235.
Tanaka, Y. et al., "Extraction of phospholipids from salmon roe with supercritical carbon dioxide and an entrainer," *J. Oleo Sci.* (2004) vol. 53, pp. 417-424.
Yamaguchi, K. et al., "Supercritical carbon dioxide extraction of oils from Antarctic krill," *J. Agr. Food Chem.* (1986) vol. 34, pp. 904-907.
Co-pending U.S. Appl. No. 12/515,098. English abstract of JP 02-215351.
English abstract of JP 04-41457.
English translation of JP 54-76858.
English translation of JP 63-162793.
English translation of JP 06-248289.
English translation of JP 08-218091.

* cited by examiner

*Primary Examiner* — Deborah D Carr
(74) *Attorney, Agent, or Firm* — Finnegan, Henderson, Farabow, Garrett and Dunner, L.L.P.

(57) ABSTRACT

The present invention relates to a process for preparing compositions of high concentrations of omega-3 fatty acids from krill. Furthermore, the invention relates to a composition comprising high concentrations of omega-3 fatty acids, and a lipid fraction from krill comprising high amounts of fatty acids with chain length C14 and C16.

31 Claims, No Drawings

KRILL OIL PROCESS

This application is a national stage filing under 35 U.S.C. §371 of International Application No. PCT/NO2009/000184 filed on May 15, 2009, which claims priority to U.S. Provisional Application No. 61/053,455 filed on May 15, 2008, the entire disclosures of which are incorporated by reference herein.

FIELD OF THE INVENTION

The present invention relates to a process for preparing compositions of high concentrations of omega-3 fatty acids from krill. Furthermore, the invention relates to a lipid fraction from krill comprising high amounts of the fatty acids with chain length C14 and C16.

BACKGROUND OF THE INVENTION

Marine phospholipids are useful in medical products, health food and human nutrition, as well as in fish feed and means for increasing the rate of survival of fish larval and fry of marine species like cod, halibut and turbot.

Phospholipids from marine organisms comprise omega-3 fatty acids. Omega-3 fatty acids bound to marine phospholipids are assumed to have particularly useful properties.

Products such as fish milt and roe are traditional raw materials for marine phospholipids. However, these raw materials are available in limited volumes and the price of said raw materials is high.

Krill are small, shrimp-like animals, containing relatively high concentrations of phospholipids. In the group Euphasiids, there is more than 80 species, of which the Antarctic krill is one of these. The current greatest potential for commercial utilization is the Antarctic *Euphausia superba*. *E. superba* has a length of 2-6 cm. Another Antarctic krill species is *E. crystallorphias*. *Meganyctiphanes norvegica*, *Thysanoessa inermis* and *T. raschii* are examples of northern krill.

Fresh hill contains up to around 10% of lipids, of that approximately 50 of % phospholipids in *Euphausia superba*. Phospholipids from krill comprise a very high level of omega-3 fatty acids, whereof the content of eicosapentaenoic acid (EPA) and docosahexaenoic acid (DHA) is above 40%. The approximate composition of lipids from the two main species of Antarctic krill is given in Table 1.

TABLE 1

Composition of krill lipids. Lipid classes, (approximate sum EPA + DHA)

|  | Wax esters | Glycerides | Phospholipids | Ratio EPA/DHA |
|---|---|---|---|---|
| *Euphausia superba* | 1 | 50 (7) | 50 (40-50) | 1.4-1.5 |
| *Euphausia crystallorphias* | 40 | 20 (4) | 40 (30-40) | 1.3 |

Furthermore, Antarctic krill has lower level of environmental pollutants than traditional fish oils.

A typical composition of commercially available krill oil is as follows:

TABLE 2

| Fatty Acid | A % |
|---|---|
| C14:0 | 19 |
| C16:0 | 22 |
| C16:1 | 13 |
| C18:0 | 1 |
| C18:1n-9 + C18:1n-7 | 25 |
| C18:2n-6 | 2 |
| C18:3n-3 | 1 |
| C20:1 | 2 |
| EPA | 4 |
| DHA | 1 |

A sample of the commercial product Superba™ Krill Oil (Aker Biomarine ASA, Norway) has been analyzed as having the following composition:

TABLE 3

| Fatty Acid | A % |
|---|---|
| C14:0 | 10 |
| C16:0 | 20 |
| C16:1 | 5 |
| C18:0 | 1 |
| C18:1n-9 + C18:1n-7 | 16 |
| C18:2n-6 | 2 |
| C18:3n-3 | 2 |
| C18:4n-3 | 5 |
| EPA | 20 |
| DHA | 12 |

The krill has a digestive system with enzymes, including lipases that are very active around 0° C. The lipases stay active after the krill is dead, hydrolyzing part of the krill lipids. An unwanted effect of this is that krill oil normally contains several percents of free fatty acids. If the krill has to be cut into smaller fragments before being processed, the person skilled in the art will immediately realize that this will increase the degree of hydrolysis. Thus, it is a desire to find a process that can utilize whole, fresh krill, or whole body parts from krill, as such a process will provide a product with improved quality and low degree of hydrolysis of lipids. This improved quality will affect all groups of krill lipids, including phospholipids, triglycerides and astaxanthin esters.

Krill lipids are to a large extent located in the animals' head. A process that can utilize fresh krill is therefore also well suited for immediate processing of the by-products from krill wherefrom the head is peeled off, a product that can be produced onboard the fishing vessel.

From U.S. Pat. No. 6,800,299 of Beaudion et al. it is disclosed a method for extracting total lipid fractions from krill by successive extraction at low temperatures using organic solvents like acetone and ethanol. This process involves extraction with large amounts of organic solvents which is unfavorable.

K. Yamaguchi et al. (*J. Agric. Food Chem.* 1986 34, 904-907) showed that supercritical fluid extraction with carbon dioxide, which is the most common solvent for supercritical fluid extraction, of freeze dried Antarctic krill resulted in a product mainly consisting of non-polar lipids (mostly triglycerides), and no phospholipids. Yamaguchi et al. reported that oil in krill meal was deteriorated by oxidation or polymerization to such an extent that only limited extraction occurred with supercritical $CO_2$.

Y. Tanaka and T. Ohkubo (*J. Oleo. Sci.* (2003), 52, 295-301) quotes the work of Yamaguci et al. in relation to their own work on extraction of lipids from salmon roe. In a more recent publication (Y. Tanaka et al. (2004), *J. Oleo. Sci.*, 53, 417-424) the same authors try to solve this problem by using a mixture of ethanol and $CO_2$ for extracting the phospholipids. By using $CO_2$ with 5% ethanol no phospholipids were removed from freeze dried salmon roe, while by adding 10% ethanol, 30% of the phospholipids were removed, and by adding as much as 30% ethanol, more than 80% of the phospholipids were removed. Freeze drying is a costly and energy consuming process, and not suited for treatment of the very large volumes of raw materials that will become available by commercial krill fisheries.

Tanaka et al. tried to optimize the process by varying the temperature of the extraction, and found that low temperatures gave the best results. 33° C., a temperature just above the critical temperature for $CO_2$, was chosen as giving best results.

Contrary to these findings, we have surprisingly found a process for extraction of a substantially total lipid fraction from fresh krill, without the need for complicated and costly pre-treatment like freeze drying of large volumes. The lipid fraction contained triglycerides, astaxanthin and phospholipids. We did not have to dry or deoil the raw material before processing. Contrary to Tanaka et al. we have found that a short heating of the marine raw material was positive for the extraction yield. It was also shown that pre-treatment like a short-time heating to moderate temperatures, or contact with a solid drying agent like molecular sieve, of the krill can make ethanol wash alone efficient in removing phospholipids from fresh krill. These findings have been the basis for the invention disclosed in International Patent Application No. PCT/NO2007/000402, which is incorporated herein by reference.

Now it has surprisingly been found that pre-treatment by microwaves on the hill raw material can be carried out before performing the process according to PCT/NO2007/000402. Microwave treatment is easily adaptable to frozen krill. When frozen krill is treated with microwaves of a suitable energy, thawing, or heating to moderate temperatures (10-30° C.) can be suitable in order to make ethanol wash alone sufficient in removing phospholipids from the hill. As described in the examples below, microwave treatment can release even more phospholipids from the hill material than heating without the use of microwaves.

The exposure to the fluid under supercritical pressure will prevent oxidation from taking place, and the combined carbon dioxide/ethanol is expected to deactivate any enzymatic hydrolysis of the hill lipids. As the process according to the invention requires a minimum of handling of the raw materials, and is well suited to be used on fresh krill, for example onboard the fishing vessel, the product according to the invention is expected to contain substantially less hydrolyzed and/or oxidized lipids than lipid produced by conventional processes. This also means that there is expected to be less deterioration of the krill lipid antioxidants than from conventional processing. The optional pre-treatment involving short-time heating of the fresh krill will also give an inactivation of enzymatic decomposition of the lipids, thus ensuring a product with very low levels of free fatty acids.

In International Patent Application No. PCT/NO2007/000402 it is provided a process for extracting a substantially total lipid fraction from fresh krill, comprising the steps of:

a) reducing the water content of krill raw material; and b) isolating the lipid fraction.

Optionally, the above-mentioned process comprising a further step of:

a-1) extracting the water reduced krill material from step a) with $CO_2$ at supercritical pressure containing ethanol, methanol, propanol or iso-propanol. This step, a-1), is performed directly after step a).

In one embodiment it is provided a process for extracting a substantially total lipid fraction from fresh krill, comprising the steps of:

a) reducing the water content of krill raw material;

a-1) extracting the water reduced krill material from step a) with $CO_2$ containing ethanol, the extraction taking place at supercritical pressure; and b) isolating the lipid fraction from the ethanol.

In a preferred embodiment, step a) comprises washing of the krill raw material with ethanol, methanol, propanol and/or iso-propanol in a weight ratio 1(krill):0.3(ethanol) to 1:5, more preferably 1:0.5 to 1:1. The washing may be performed using all the ethanol in one operation, or by dividing the total amount of ethanol between several sequential steps.

Preferably, the krill raw material is heated to 60-100° C., more preferred to 70-100° C., and most preferred to 80-95° C., before washing. Furthermore, the hill raw material is preferably heated for about 1 to 40 minutes, more preferred about 1 to 15 minutes, and most preferred for about 1 to 5 minutes, before washing.

In another preferred embodiment of the invention fresh or frozen hill are treated with microwaves before washing.

After washing, the alcohol will contain krill lipids, including a significant part of the krill phospholipids.

In another embodiment, step a) comprises bringing the hill raw material in contact with molecular sieve or another form of membrane, such as a water absorbing membrane or a water permeable membrane, for removal of water.

Preferably, the amount of ethanol, methanol, propanol and/or iso-propanol in step a-1) is 5-20% by weight, more preferably 10-15% by weight.

In addition to producing a product containing the total lipids of hill, phospholipids can be separated from the other lipids. To separate the total lipids obtained by extraction at supercritical pressure, according to the present invention into the different lipid classes, extraction of the said total lipids with pure carbon dioxide can remove the non-polar lipids from the omega-3 rich phospholipids. Extraction of the total lipids with carbon dioxide containing less than 5% ethanol or methanol is another option.

As the phospholipids are much richer in the valuable omega-3 fatty acids than the other lipid classes, high concentrates of omega-3 fatty acids can be produced. While commercially available fish oils comprise 11-33% total omega-3 fatty acids (Hjaltason, B and Haraldsson, G G (2006) Fish oils and lipids from marine sources, In: *Modifying Lipids for Use in Food* (F D Gunstone, ed), Woodhead Publishing Ltd, Cambridge, pp. 56-79), the phospholipids of hill contain much higher levels (Ellingsen, T E (1982) Biokjemiske studier over antarktisk hill, PhD thesis, Norges tekniske hoyskole, Trondheim. English summary in Publication no. 52 of the Norwegian Antarctic Research Expeditions (1976/77 and 1978/79)), see also Table 1.

The omega-3 rich phospholipids can be used as they are, giving the various positive biological effects that are attributed to omega-3 containing phospholipids. Alternatively, the phospholipids can be transesterified or hydrolyzed in order to give esters (typically ethyl esters) or free fatty acids or other derivatives that are suitable for further concentration of the omega-3 fatty acids. As examples, the ethyl esters of krill phospholipids will be valuable as an intermediate product for producing concentrates that comply with the European Pharmacopoeia monographs no. 1250 (Omega-3-acid ethyl ester 90), 2062 (Omega-3-acid ethyl esters 60) and 1352 (Omega-3-acid triglycerides). At the same time, the remaining lipids (astaxanthin, antioxidants, triglycerides, wax esters) can be used as they are for various applications, including feed in aquaculture, or the lipid classes can be further separated.

Compositions comprising high concentrations of omega-3 fatty acids are useful as pharmaceuticals for instance in the treatment of hypertriglyceridemia, dyslipidemia, hypercholesterolemia, heart failure, arterial fibrillation, coronary heart disease (CHD), vascular disease, atherosclerotic disease and related conditions, and the prevention or reduction of cardiovascular and vascular events.

Such compositions are K85EE or AGP (Pronova BioPharma ASA, Norway) which is the lipid composition in drug products like Omacor®, Lovaza™ and Seacor®. In this regard, in one embodiment, reference is made to U.S. Pat. No. 5,656,667 of Breivik et al. and possible fatty acids compositions disclosed therein.

In another embodiment, a pharmaceutical omega-3 fatty acid ethyl ester lipid composition comprises the following characteristics:

TABLE 4

| Test | Minimum Value | Maximum Value |
| --- | --- | --- |
| EPA EE[1] (C20:5) | 430 mg/g | 495 mg/g |
| DHA EE[1] (C22:6) | 347 mg/g | 403 mg/g |
| EPA EE[1] and DHA EE[1] | 800 mg/g | 880 mg/g |
| Total n-3 fatty acids | 90% (w/w) | |

[1]EE is short for ethyl ester; i.e. EPA EE = EPA ethyl ester, and DHA EE = DHA ethyl ester.

Normally, K85EE and other compositions comprising very high concentrations of omega-3 fatty acids will have to be prepared by a combination of techniques, some of which work according to chain length (short path distillation, also called molecular distillation) and others which work according to degree of unsaturation (urea fractionation).

The processes short path distillation and molecular distillation are regarded as identical processes, the main issue being that the vacuum is high in order to keep the temperature low enough to avoid decomposition of the thermolabile polyunsaturated fatty acids. As used herein, the terms "thin-film distillation" and "falling-film distillation" are included in the term "short path distillation".

We have now very surprisingly found that the krill lipids can be used to produce compositions like K85EE without using separation techniques that work according to degree of unsaturation (urea fractionation), or by only minor use of such techniques. By significantly reducing the amounts of urea that are needed for the production of K85EE, the yields are substantially increased and the cost of production is substantially reduced.

SUMMARY OF THE INVENTION

It is a main object of the present invention to provide a process for preparing compositions comprising high concentrations of omega-3 fatty acids without using separation techniques that work according to degree of unsaturation (urea fractionation), or by only minor use of such techniques.

This and other objects are obtained by the process and composition as defined in the accompanying claims.

DETAILED DESCRIPTION OF THE INVENTION

According to the invention it is provided a process for preparing compositions comprising high concentrations of omega-3 fatty acids, comprising the step of subjecting a lipid fraction from krill obtained according to International Patent Application No. PCT/NO2007/000402 as described above, to short path distillation, or to one or more steps of supercritical fluid extraction, chromatography, or a combination thereof.

In a preferred embodiment of the invention fresh or frozen krill are treated with microwaves before washing.

In another preferred embodiment of the invention the short path distillation is a one-step or two-step short path distillation, preferably a two-step short path distillation.

In an embodiment of the invention a two-step short path distillation as disclosed in International Patent Application No. PCT/IB2003/002827 is performed.

Optionally, the above-mentioned process comprises a further step of mild urea fractionation, and possibly a final short path distillation.

Mild urea fractionation means a process where saturated and monounsaturated fatty acid esters are removed from a mixture of fatty acid esters by complexation with urea crystallizing from a solution in ethanol and where the amount of urea is less than otherwise required for omega-3 ester concentrates produced by short path distillation of fish oils. An omega-3 concentrate with the fatty acid composition described in Table 5 below can be processed with urea fractionation with a urea/ethyl ester ratio of preferably 0.1-1.5, more preferably 0.5-1.0.

In yet another embodiment of the invention, one or more steps of supercritical fluid extraction, chromatography, or a combination thereof are performed. Optionally mild urea fractionation is performed before or after the said steps.

Furthermore, a composition of high concentrations of omega-3 fatty acids obtainable by the above-mentioned process is provided by the present invention.

In an aspect of the invention the composition of high concentrations of omega-3 fatty acids comprises at least 75 weight % of eicosapentaenoic acid (EPA) and/or docosahexaenoic acid (DHA), more preferred 80 weight % of EPA and DHA.

In another aspect of the invention the composition of high concentrations of omega-3 fatty acids comprises a combination of EPA and DHA.

In a further aspect of the invention the EPA and/or DHA in the composition of high concentrations of omega-3 fatty acids are present as ethyl esters.

The composition of the invention may be the pharmaceutical composition defined in the Label for Lovaza™ or Omacor®.

According to the invention the composition may comprise high concentrations of omega-3 fatty acids and low concentrations of omega-6 fatty acids. The omega-3/omega-6 ratio is preferably>30, more preferably>40, and most preferably>50.

In an aspect of the invention the concentration of the fatty acid C22:5 n-6 of the composition is below 0.8%.

Furthermore, the invention provides a lipid fraction from krill, comprising: fatty acids with chain length C14 and C16 in an amount of >25 weight %; and EPA and/or DHA in an amount of >30 weight %. Preferably, the amount of EPA and/or DHA in the lipid fraction is >35 weight %, more preferably >40 weight %.

In another preferred embodiment of the invention, the lipid fraction is substantially free from the fatty acid C22:5 n-6.

In another preferred embodiment of the invention, the lipid fraction is a krill oil supplement product.

In another preferred embodiment of the invention, the lipid fraction is used as a start material in further process steps in order to achieve a high concentrate omega-3 acid or ester product.

In a further aspect of the present invention, the use of a lipid fraction as mentioned above as start material to achieve an omega-3 supplement product or a pharmaceutical composition, is provided.

The process of the present invention can be performed with a wide variety of processing conditions, some of which are exemplified below.

In the following "fresh" krill is defined as krill that is treated immediately after harvesting, or sufficiently short time after harvesting to avoid quality deterioration like hydrolysis or oxidation of lipids, or krill that is frozen immediately after harvesting. Fresh krill can be the whole krill, or by-products from fresh krill (i.e. after peeling). Fresh krill can also be krill, or by-products from krill, that have been frozen shortly after harvesting.

EXAMPLES

Table 5 shows that the ethanol extracts produced according to the process of International Patent Application No. PCT/NO2007/000402 and according to the present invention, comprise mainly phospholipids, which are very rich in omega-3 fatty acids.

Sample No. EO-014 (without pre-heating) is slightly more rich in these acids than sample No. EO-013 which is produced with pre-heating. However, this is more than compensated for by the higher yield of the latter sample.

Sample No. 132-1 (is frozen hill that) has been treated with microwaves until thawing and a temperature of 18° C. A sample that was further heated by microwaves to 82° C. gave a similar result. It was observed that this microwave treatment gave a yield of 5% in the ethanol extract. By mild pressing of the ethanol washed hill an additional amount of liquid was obtained. After removal of ethanol and water a dry extract of 1.3% compared to the starting krill weight was obtained (sample 132-1). It is interesting to note that this fraction was very low in EPA and DHA, consistent with this fraction being low in phospholipids and high in triglycerides. The skilled person will from these results realize that by removing ethanol very carefully, minimizing the physical stress on the krill residues, a first extract that is even higher in omega-3 fatty acids than sample 132-1 might be obtained. The skilled person will also realize that the separation by simple ethanol extraction in two extracts with very different fatty acid contents—one rich in omega-3 acids and one low in omega-3 acids—is a surprising effect that can only be obtained based on fresh or frozen krill. A procedure based on hill meal will not form the basis for differentiation of fatty acid content based on a simple pressing procedure, as illustrated in this example. The person skilled in the art will realize that the second extract can be obtained by removing of ethanol from the residual hill material by a number of procedures, e.g. pressing or centrifugation. Furthermore, the skilled person will realize that the production of a second extract as described above also will be applicable to pre-treatments as disclosed in International Patent Application No. PCT/NO2007/000402.

The person skilled in the art will realize that when a second extract is obtained as described above, less solvent will be needed in order to remove residual lipids by extracting with carbon dioxide or carbon dioxide and co-solvents as disclosed in International Patent Application No. PCT/NO2007/000402. This is an additional benefit from making two ethanol extracts as described above.

TABLE 5

| Sample No. | | EO-013 | EO-014 | 132-1 | 132-2 |
| --- | --- | --- | --- | --- | --- |
| Krill | kg | 6 | 6 | | Lipids obtained by mild pressing of 132-1 |
| Ethanol | kg | 6 | 6 | | |
| Conditions | | Pre-heating | No pre-heating | Microwave[1] | |
| Amount | Gram | | | | |
| EtOH | | | | 5.0% | 1.3% |
| Extract | g | 215 (3.6%) | 112 (1.9%) | | |
| C14:0 | A % | 5.2 | 3.7 | 6.4 | 17.9 |
| C16:0 | A % | 23.5 | 21.0 | 24.5 | 22.8 |
| C16:1n-7 | A % | 3.8 | 3.2 | 4.5 | 12.0 |
| C16:4n-1 | A % | 0.3 | | 0.3 | 0.8 |
| C18:0 | A % | 1.0 | 0.8 | 0.9 | 1.5 |
| C18:1n-9 | A % | 6.1 | 5.1 | 6.7 | 15.7 |
| C18:1n-7 | A % | 6.2 | 5.9 | 7.1 | 7.6 |
| C18:2n-6 | A % | 2.0 | 2.2 | 1.8 | 1.7 |
| C18:3n-3 | A % | 1.0 | 1.1 | 0.8 | 0.5 |
| C18:4n-3 | A % | 1.7 | 2.0 | 1.5 | 1.9 |
| C20:1 | A % | 0.5 | 0.5 | 0.4 | 1.2 |
| C20:4n-6 | A % | 0.9 | 1.2 | 0.6 | 0.2 |
| C20:4n-3 | A % | 0.7 | 0.8 | 0.4 | 0.3 |
| EPA | A % | 29.2 | 31.1 | 27.9 | 7.7 |
| C22:1 | A % | 0.9 | 0.9 | 0.8 | 0.4 |
| C21:5n-3 | A % | 0.6 | 0.7 | 0.6 | 0.1 |
| C22:5n-3 | A % | 0.7 | 0.7 | 0.6 | 0.1 |
| DHA | A % | 13.8 | 15.5 | 12.1 | 3.2 |

[1] The results in Table 5 were obtained by derivatization of the extracts by a procedure similar to that given for triglycerides in the European Pharmacopoeia monograph 2.4.29, Composition of fatty acids in oils rich in omega-3-acids. For the less experienced person, a guide to identification of fatty acids can be found from the Type Chromatogram of the European Pharmacopoeia monograph 1912, 'Fish oil, rich in omega-3 acids.'

Sample No. EO-013 contains 47.7% (GC area) of omega-3 fatty acids. Sample No. 132-1 contains 43.9% (GC area) omega-3 fatty acids. By using a conventional method the fatty acids can be ethylated, and the person known in the art will realize that after removal of polar and inorganic components, and if necessary purification by short path distillation or similar acting techniques, the resulting ethyl ester product will contain close to 50% omega-3 fatty acids.

A surprising observation from Table 5 is that the krill lipids are substantially without the polyunsaturated fatty acid C22:5n-6.

Another surprising observation from Table 5 is the high concentration of C14 and C16 fatty acids (a total of 32.8% in sample No. EO-013, 35.7% in sample No. 132-1). This makes the ethyl esters surprisingly suitable for treatment by separation techniques which separate according to chain length. One example of such a separation technique is short path distillation. By using a technique that removes approx. 96% of the C14 acids, approx. 90% of the C16 acids, and approx. 50% of the C18 acids as compared to C20-C22 fatty acids, a product with the following relative composition is obtained:

TABLE 6

| Fatty acid | GC A % |
| --- | --- |
| C14:0 | 0.3 |
| C16:0 | 3.9 |
| C16:1 | 0.6 |
| C16:4n-1 | 0.1 |
| C18:0 | 0.8 |
| C18:1n-9 | 5.1 |
| C18:1n-7 | 5.2 |
| C18:2n-6 | 1.7 |
| C18:3n-3 | 0.8 |
| C18:4n-3 | 1.5 |
| C20:1 | 0.8 |
| C20:4n-6 | 1.5 |

TABLE 6-continued

| Fatty acid | GC A % |
|---|---|
| C20:4n-3 | 1.2 |
| EPA | 48.7 |
| C22:1 | 1.5 |
| C21:5n-3 | 1.0 |
| C22:5n-3 | 1.2 |
| DHA | 23.0 |

Sum omega-3 fatty acids: 77.3 A %

It is interesting to note that the krill oil seems to be free of the fatty acid C22:5 n-6.

The person known in the art will know that this fraction can be purified further, for example by a two-step short path distillation according to known procedures, removing most of the fatty acids with chain length below C20, as well as some of the C20 fatty acids, while leaving most of the C22 fatty acids in the product. The person known in the art would realize that such a procedure would lead to compositions complying with K85EE.

An example of such a composition is obtained by removing approx. 90% of C14, approx. 80% of C16, approx. 55% of C18, approx. 25% of C20 compared to the C22 fatty acids, as shown in Table 7 below. The person known in the art will realize that even better separations can be obtained, depending on separation method and the desired yield.

TABLE 7

| | GC A % |
|---|---|
| C16:0 | 1.1 |
| C16:1 | 0.2 |
| C18:0 | 0.2 |
| C18:1n-9 | 1.4 |
| C18:1n-7 | 1.4 |
| C18:2n-6 | 0.5 |
| C18:3n-3 | 0.2 |
| C18:4n-3 | 0.4 |
| C20:1 | 0.9 |
| C20:4n-6 | 1.6 |
| C20:4n-3 | 1.3 |
| EPA | 52.4 |
| C22:1 | 2.2 |
| C21:5n-3 | 1.3 |
| C22:5n-3 | 1.7 |
| DHA | 32.9 |

Sum omega-3 fatty acids: 90.2 A %

The product obtained in the ethanol extract can be defatted using supercritical fluid technology in a similar way as disclosed in International Patent Application N. PCT/NO2007/000402. The person skilled in the art will realize that this will lead to a starting material even higher in omega-3 fatty acids than samples Nos. EO-013 and EO-014, for example samples containing up to or above 55% omega-3 fatty acids. Such products could be utilized to produce compositions like K85EE in an even simpler fashion, and with higher yield than described above.

Below, a composition based on krill lipids (from Table 7) is compared with a typical K85EE composition:

TABLE 8

| | (GC A %) | |
|---|---|---|
| | From krill | K85EE |
| C16:0 | 1.1 | nd |
| C16:1 | 0.2 | nd |

TABLE 8-continued

| | (GC A %) | |
|---|---|---|
| | From krill | K85EE |
| C18:0 | 0:2 | nd |
| C18:1n-9 | 1.4 | 0.03 |
| C18:1n-7 | 1.4 | nd |
| C18:2n-6 | 0.5 | 0.1 |
| C18:3n-3 | 0.2 | 0.1 |
| C18:4n-3 | 0.4 | 2.1 |
| C20:1 | 0.9 | nd |
| C20:4n-6 | 1.6 | 2.3 |
| C20:4n-3 | 1.3 | 0.8 |
| Furan acid 8 | nd | 0.4 |
| EPA | 52.4 | 47.3 |
| C22:1 | 2.2 | nd |
| C21:5n-3 | 1.3 | 2.1 |
| C22:5n-6 | nd | 1.0 |
| C22:5n-3 | 1.7 | 3.3 |
| DHA | 32.9 | 38.3 |

(nd = not detected)

A surprising observation from Table 8 is that the krill lipids contain substantially lower amounts of the polyunsaturated fatty acids C18:4n-3, C22:5n-3 and C22:5n-6 than the K85EE composition.

After mild urea fractionation in order to remove saturated and monounsaturated fatty acid ethyl esters, followed by final short path distillation, the fatty acid composition of Table 6 and 7/8 can be concentrated to compositions as described in Table 9:

TABLE 9

| | (GC A %) | | |
|---|---|---|---|
| | From Table 6 | From Table 7/8 | K85EE |
| C16:0 | nd | nd | nd |
| C16:1 | nd | nd | nd |
| C18:1n-9 | 0.2 | 0.1 | 0.03 |
| C18:1n-7 | 0.2 | 0.1 | nd |
| C18:2n-6 | 0.2 | 0.1 | 0.1 |
| C18:3n-3 | 0.6 | 0.2 | 0.1 |
| C18:4n-3 | 1.2 | 0.4 | 2.1 |
| C20:1 | nd | nd | nd |
| C20:4n-6 | 1.6 | 1.6 | 2.3 |
| C20:4n-3 | 1.3 | 1.3 | 0.8 |
| Furan acid 8 | nd | nd | 0.4 |
| EPA | 52.7 | 53.4 | 47.3 |
| C22:1 | 0.1 | 0.1 | nd |
| C21:5n-3 | 1.5 | 1.5 | 2.1 |
| C22:5n-6 | nd | nd | 1.0 |
| C22:5n-3 | 1.9 | 2.0 | 3.3 |
| DHA | 38.5 | 39.0 | 38.3 |
| Sum n-3 | 97.7 | 97.9 | 94.0 |

(nd = not detected)

However, it seems that the total omega-3 content of the urea fractionated products from krill oil will be significantly higher than that of K85EE. The main reason for this difference is that hill oil surprisingly seems to lack C22:5 n-6. This means that the omega-3/omega-6 ratio of the compositions from krill oil phospholipids is significantly higher than those obtained in concentrates based on fish oils. Thus the omega-3/omega-6 ratio is as high as approx. 54 to approx 58 in the two compositions based on hill oil in Table 8. The person known in the art will immediately realize that this ratio is much higher than those obtained in products from fish oils.

The exact compositions will depend on the distillation conditions. The conditions can be altered so as to obtain flexible EPA/DHA ratios. However, if the EPA/DHA ratio in the final product will deviate much from the ratio in the starting krill oil, this can only be obtain at the cost of lowering the overall yields. However, the distillate not utilized in the composition comprising high concentrations of omega-3 fatty acids, can be valuable for production of other compositions containing omega-3 fatty acids.

As can be seen from Table 9, the products that can be produced from the compositions of Table 6 and 7/8 may be virtually identical, the only difference being that somewhat more urea is required when concentrating compositions according to Table 6 than when concentrating compositions according to Table 7/8. On the other hand, starting with compositions according to Table 6 can result in higher overall yields than starting with compositions according to Table 7/8. It will also be possible to start directly with urea fractionation of the ethyl esters of phospholipids of krill oil, without having to perform an initial concentration step with short path distillation or similar techniques.

The person known in the art will realize that some of the valuable long-chain C20-C22 omega-3 fatty acids will be lost in the solid adducts that are formed by urea fractionation. This is especially the case when high urea/ethyl ester ratios are used. By starting with esters from hill phospholipids, the relative amounts of urea can be significantly reduced, thus also reducing the losses of long-chain omega-3 fatty acids during this concentration step.

The invention shall not be limited to the shown embodiments and examples.

The invention claimed is:

1. A process for preparing a composition comprising a high concentration of omega-3 fatty acids, the process comprising:
   a) reducing the water content of a krill raw material;
   b) isolating the lipid fraction from the krill raw material to obtain a substantially total lipid fraction
   c) subjecting the lipid fraction to an ethylation step to form ethyl esters; and
   d) subjecting the lipid fraction to short path distillation or to one or more steps of supercritical fluid extraction, chromatography, or a combination thereof.

2. The process of claim 1, wherein step a) comprises washing the krill raw material with at least one alcohol chosen from ethanol, methanol, propanol, iso-propanol, and any combination thereof in a weight ratio of krill material:alcohol ranging from 1:0.5 to 1:5; and step b) comprises isolating the lipid fraction from the at least one alcohol.

3. The process of claim 2, wherein step a) comprises washing the krill raw material with ethanol; and step b) comprises isolating the lipid fraction from the ethanol.

4. The process of claim 1, further comprising the step:
   a-1) extracting the water reduced krill raw material from step a) with $CO_2$ at supercritical pressure containing at least one alcohol chosen from ethanol, methanol, propanol, iso-propanol, and a combination thereof;
   wherein step a-1) is performed after step a) and before step b).

5. The process of claim 2, wherein the krill raw material is heated to a temperature ranging from 60° C. to 100° C. before washing with the at least one alcohol.

6. The process of claim 5, wherein the krill raw material is heated to a temperature ranging from 70° C. to 100° C. before washing with the at least one alcohol.

7. The process of claim 6, wherein the krill raw material is heated to a temperature ranging from 80° C. to 95° C. before washing with the at least one alcohol.

8. The process of claim 1, wherein the krill raw material is pre-treated by use of microwaves before washing.

9. The process of claim 2, wherein washing the krill raw material with the at least one alcohol in step a) produces an extract rich in omega-3 fatty acids, and
   removing residual alcohol from the krill material in step b) produces an extract low in omega-3 fatty acids.

10. The process of claim 9, wherein the removal of residual alcohol from the krill material in step b) is carried out by pressing, centrifugation, or a combination thereof.

11. The process of claim 1, wherein the short path distillation is a one-step or two-step short path distillation.

12. The process of claim 1, further comprising the step:
    e) subjecting the lipid fraction of step d) to mild urea fractionation.

13. The process of claim 12, wherein the urea to ethyl ester ratio ranges from 0.1 to 1.5.

14. The process of claim 13, wherein the urea to ethyl ester ratio ranges from 0.5 to 1.0.

15. The process of claim 12, further comprising the step:
    f) subjecting the lipid fraction of step e) to short path distillation.

16. A composition derived from krill comprising at least 75% by weight of at least one of eicopentaenoic acid (EPA) and docosahexaenoic acid (DHA), wherein the omega-3/omega-6 fatty acid ratio is greater than 30.

17. The composition of claim 16, wherein the composition comprises at least 80% by weight of at least one of EPA and DHA.

18. The composition of claim 16, wherein the composition comprises at least 90% by weight of omega-3 fatty acids.

19. The composition of claim 17, wherein the weight ratio of EPA to DHA ranges from 1:2 to 2:1.

20. The composition of claim 16, wherein the composition comprises a combination of EPA and DHA.

21. The composition of claim 16, wherein at least one of the EPA and DHA is present in acid or ethyl ester form.

22. The composition of claim 16, wherein the omega-3/omega-6 fatty acid ratio is greater than 40.

23. The composition of claim 22, wherein the omega-3/omega-6 fatty acid ratio is greater than 50.

24. The composition of claim 16, wherein the concentration of the fatty acid C22:5 n-6 is below 0.8% by weight with respect to the total composition weight.

25. A lipid fraction from krill comprising:
    greater than 25% by weight of at least one fatty acid with a chain length chosen from C14 and C16, with respect to the total lipid fraction weight; and
    greater than 30% by weight of at least one of eicosapentaenoic acid (EPA) and docosahexaenoic acid (DHA) with respect to the total lipid fraction weight.

26. The lipid fraction of claim 25, comprising greater than 35% by weight of at least one of EPA and DHA with respect to the total lipid fraction weight.

27. The lipid fraction of claim 25, comprising greater than 40% by weight of at least one of EPA and DHA with respect to the total lipid fraction weight.

28. The lipid fraction of claim 25, wherein the lipid fraction is substantially free from the fatty acid C22:5 n-6.

29. A krill oil supplement product comprising the lipid fraction of claim 25.

30. The process of claim 1, wherein the lipid fraction is used as a start material in further process steps in order to achieve a high concentrate omega-3 acid or ester product.

31. The process of claim 30, wherein the high concentrate omega-3 acid or ester product is an omega-3 supplement product or a pharmaceutical composition.

* * * * *